United States Patent [19]

Mische et al.

[11] Patent Number: 5,052,105

[45] Date of Patent: Oct. 1, 1991

[54] MICRO-CABLE INTERCONNECT

[75] Inventors: Hans A. Mische, St. Cloud; Wallace J. Devries, New Germany; John M. Hokanson, Hutchinson; Daniel J. Klima, St. Cloud; Steven P. Mertens, Hutchinson, all of Minn.

[73] Assignee: Hutchinson Technology, Inc., Hutchinson, Minn.

[21] Appl. No.: 533,131

[22] Filed: Jun. 5, 1990

[51] Int. Cl.$^5$ .......................................... H01R 43/00
[52] U.S. Cl. ...................... 29/883; 79/857; 118/691; 156/55; 174/117 F
[58] Field of Search ............... 29/857, 883; 427/117, 427/120, 54.1; 134/38; 118/325, 420, 641; 174/117 F; 156/55

[56] References Cited

U.S. PATENT DOCUMENTS

| | | | |
|---|---|---|---|
| 3,540,956 | 11/1970 | Arnold et al. | 156/54 |
| 3,547,718 | 12/1970 | Gordon | 156/55 |
| 3,612,744 | 10/1971 | Thomas | 174/36 |
| 3,673,982 | 7/1972 | Rutledge et al. | 118/641 |
| 3,757,029 | 9/1973 | Marshall | 174/36 |
| 3,794,522 | 2/1974 | Mueller et al. | 174/117 F X |
| 3,802,974 | 4/1974 | Emmel | 156/55 |
| 3,833,755 | 9/1974 | Soelberg | 174/117 F |
| 3,951,713 | 4/1976 | Emmel | 156/52 |
| 4,000,348 | 12/1976 | Harlow | 428/422 |
| 4,090,902 | 5/1978 | Ferrentino et al. | 156/177 |
| 4,096,010 | 6/1978 | Parham et al. | 156/179 |
| 4,097,324 | 6/1978 | Emmel | 156/179 |
| 4,098,628 | 7/1978 | Walton | 156/52 |
| 4,150,929 | 4/1979 | Brandt | 425/114 |
| 4,165,559 | 8/1979 | Lang et al. | 156/55 X |
| 4,190,319 | 2/1980 | Eggleston | 350/96.23 |
| 4,288,916 | 9/1981 | Verma | 29/828 |
| 4,310,365 | 1/1982 | Elliott et al. | 156/55 |
| 4,364,788 | 12/1982 | Bloodworth, Jr. | 156/179 |
| 4,367,585 | 1/1983 | Elliott et al. | 29/857 |
| 4,406,915 | 9/1983 | Lang | 174/117 F |
| 4,407,298 | 10/1983 | Lentz et al. | 128/713 |
| 4,417,886 | 11/1983 | Frankhouser et al. | 604/53 |
| 4,423,282 | 12/1983 | Suzuki et al. | 174/36 |
| 4,443,657 | 4/1984 | Hill et al. | 174/110 |

(List continued on next page.)

FOREIGN PATENT DOCUMENTS 46-38225 10/1971 Japan .................................. 427/120
1090754 5/1984 U.S.S.R. .............................. 118/420

OTHER PUBLICATIONS

Rima, "Basics of Tape Automated Bonding," Hybrid Circuit Technology, Nov. 1984, Describes General Information on Integrated Circuit Bonding.
Feindel, "Approach to Product Assembly," Connection Technology, Mar. 1986, Describes General Information on Integrated Circuit Bonding.
Schwartz, "Chip-on-Board: Shrinking Surface Mount," Assembly Engineering, Mar. 1987, Describes General Information on Integrated Circuit Bonding.

Primary Examiner—Carl J. Arbes
Attorney, Agent, or Firm—Faegre & Benson

[57] ABSTRACT

A micro-cable interconnect comprises a single exterior flexible insulative coating internally containing a plurality of terminally prepared, precisely spaced conductors. The conductors are arranged with a spacing and pitch to identically match spacing and pitch of interconnect zones operatively connected to an integrated circuit or connector, with the conductors constructed and arranged for bonding to the interconnect zones. A method of forming a micro-cable interconnect comprises the steps of:

(a) providing a continuous formation of conductors of precisely controlled spacing and tension to identically match spacing of interconnect zones operatively connected to an integrated circuit or connector to which the conductors are constructed and arranged for attachment;

(b) applying coating precursor to selected lengths of the formation of conductors and providing curing to the selected lengths to provide cured and uncured portions; and (c) cutting the conductors at the uncured portions to form micro-cable interconnect.

10 Claims, 6 Drawing Sheets

U.S. PATENT DOCUMENTS

| | | | |
|---|---|---|---|
| 4,460,427 | 7/1984 | Haney et al. | 156/303 |
| 4,468,089 | 8/1984 | Brorein | 350/96.23 |
| 4,484,586 | 11/1984 | McMickle et al. | 128/786 |
| 4,515,592 | 5/1985 | Frankhouser | 604/163 |
| 4,581,291 | 4/1986 | Bongianni | 428/381 |
| 4,600,805 | 7/1986 | Glynn et al. | 174/102 R |
| 4,626,298 | 12/1986 | Allard | 156/55 |
| 4,692,566 | 9/1987 | Kauffman | 174/117 FF |
| 4,744,631 | 5/1988 | Eichenbaum et al. | 350/96.23 |
| 4,761,519 | 8/1988 | Olson et al. | 174/107 |
| 4,815,471 | 5/1989 | Stobie | 128/675 |
| 4,834,710 | 5/1989 | Fleck | 604/171 |
| 4,861,945 | 8/1989 | Buck et al. | 174/69 |

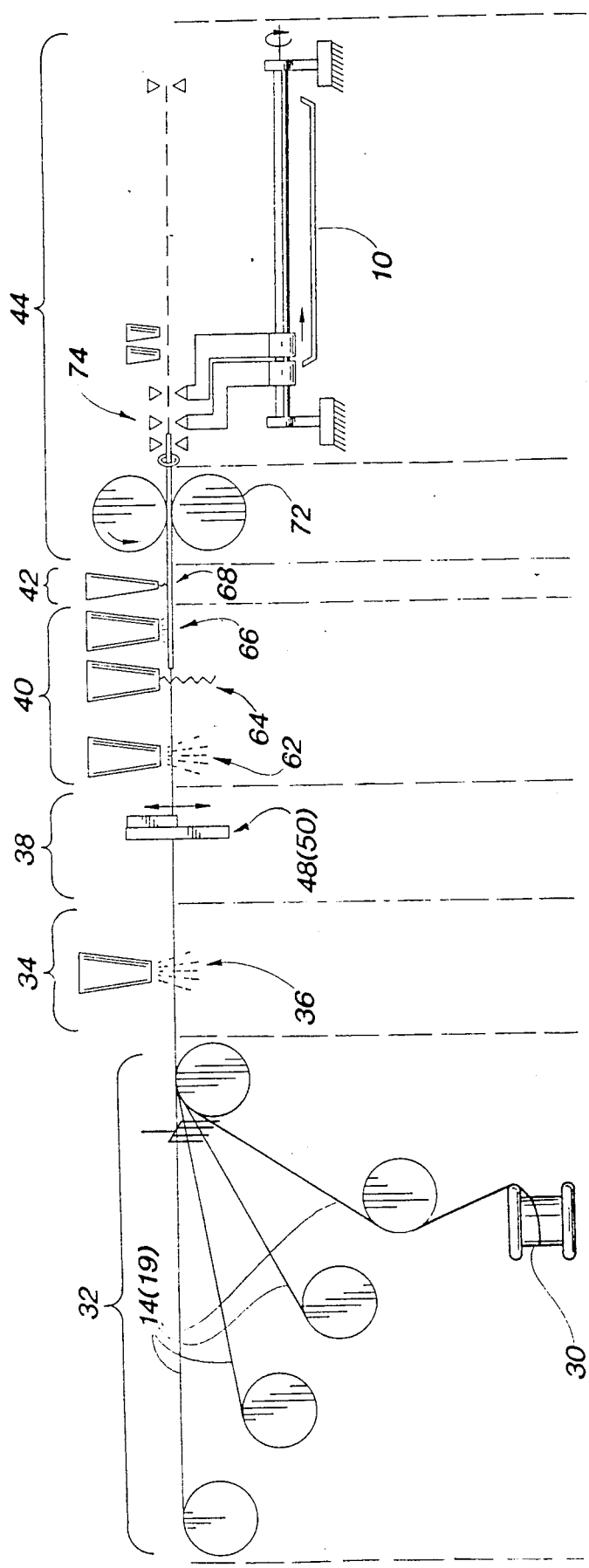

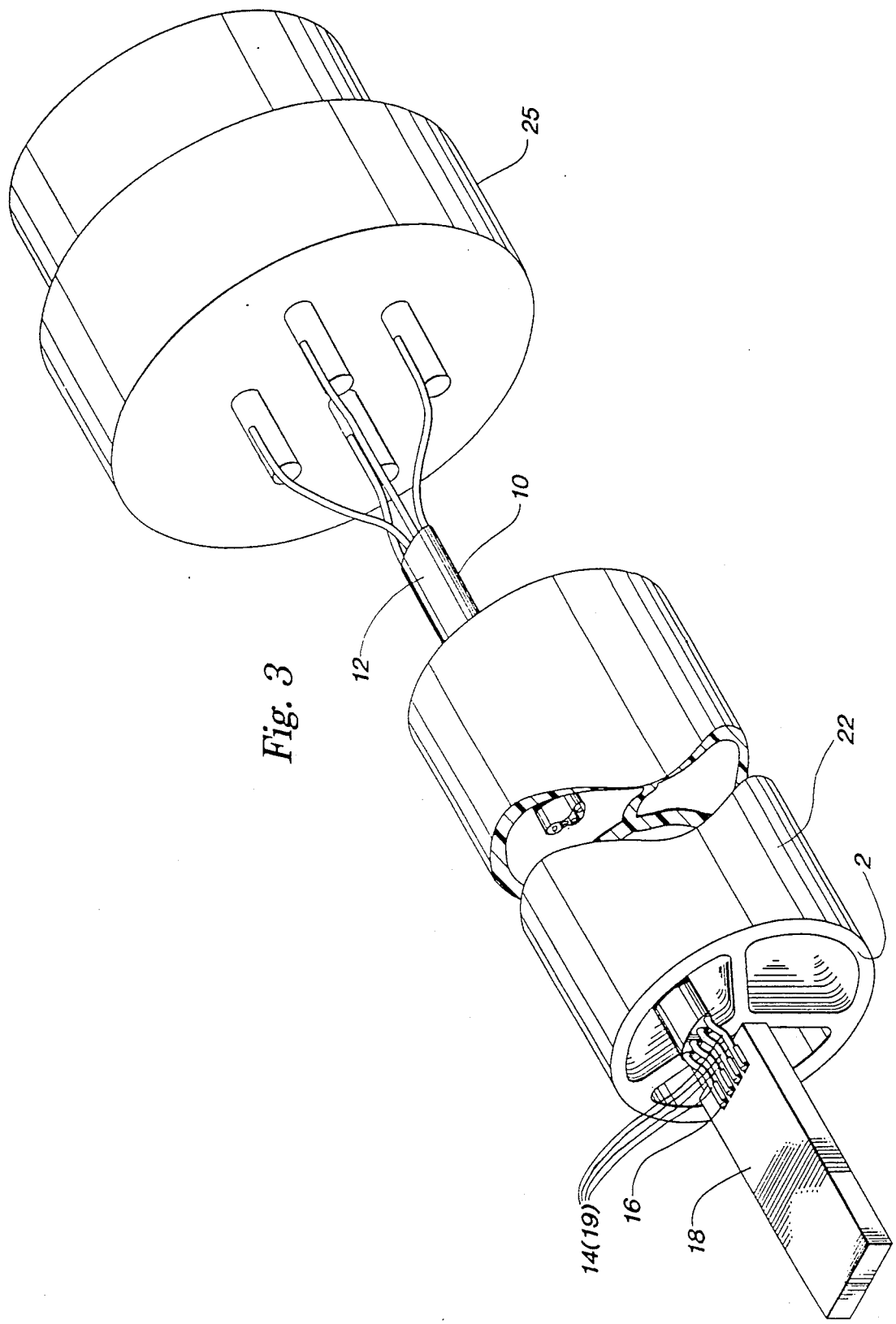

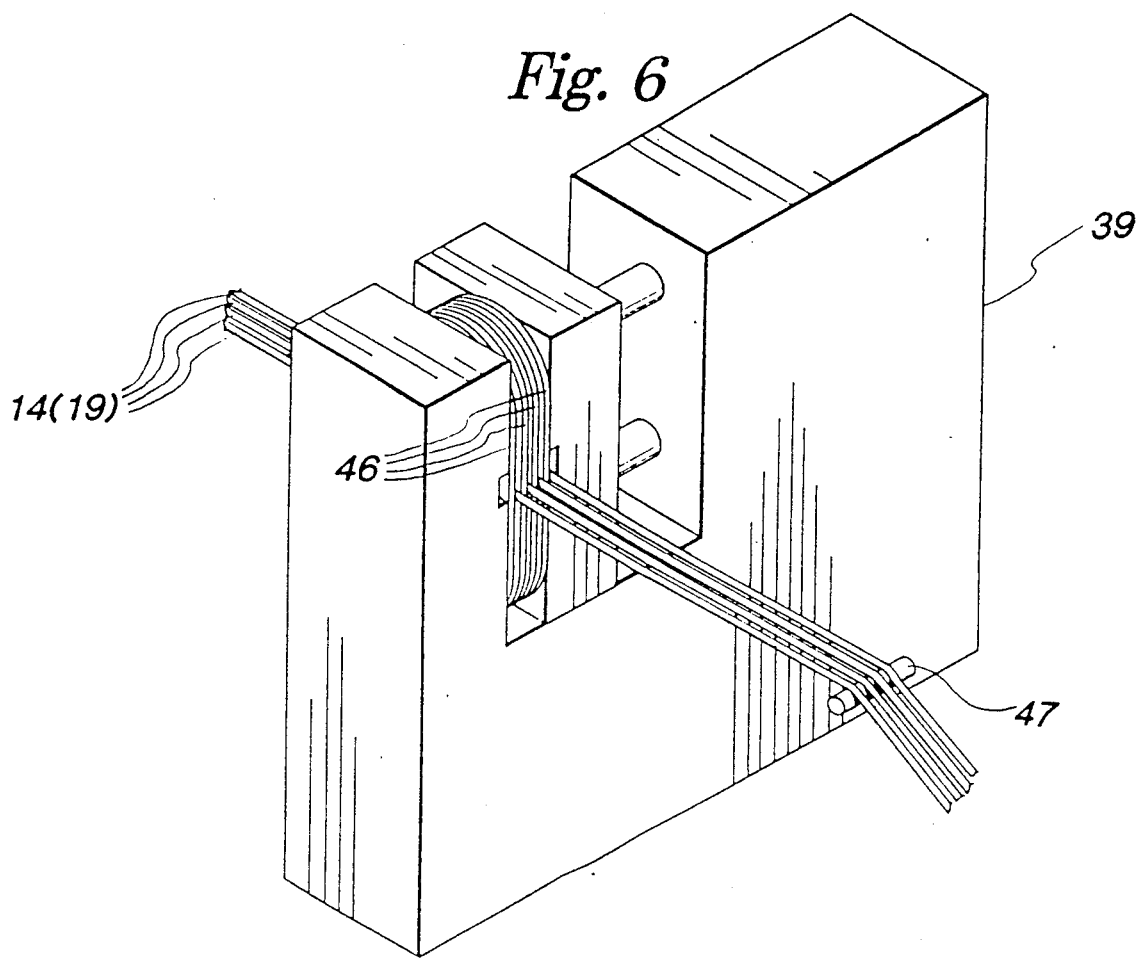
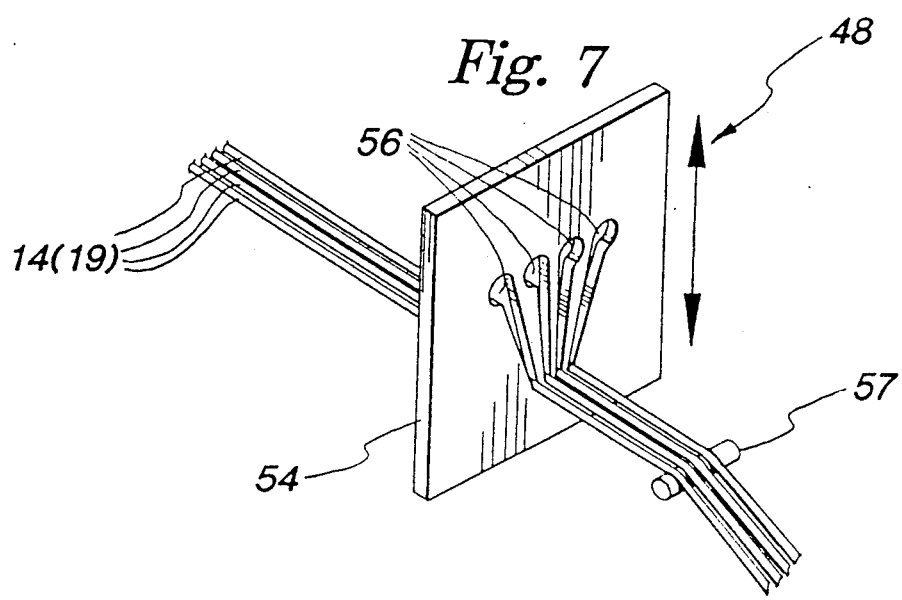

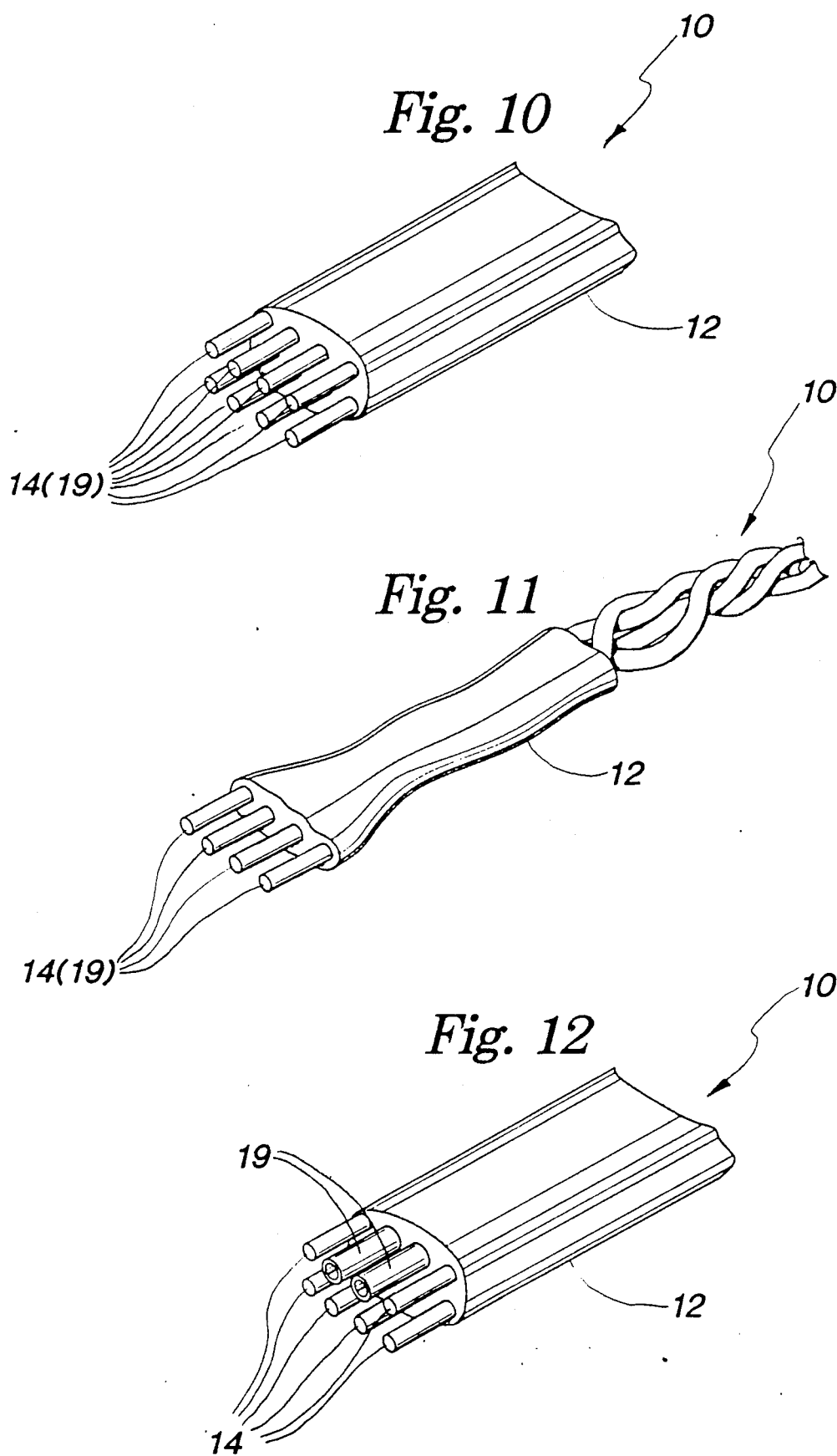

MICRO-CABLE INTERCONNECT

FIELD OF THE INVENTION

This invention is directed to a micro-cable interconnect which is a single, multiconductor cable constructed for connection to interconnect zones of an integrated circuit and conduction of the signals therefrom to a connector. More particularly, the micro-cable interconnect of this invention is suitable for use in diagnostic catheters for in vivo sensing of certain body parameters by coupling signals from a sensor, located at the catheter's distal end within a patient's body, to a connector located at the catheter's proximal end, outside the body. The micro-cable interconnect has exposed, precisely spaced conductors with the identical pitch as the sensor's pads, facilitating automatic attachment. The interconnect's flexible one piece micro-construction allows it to be inserted into the catheter lumen with greater ease and less damage than individual wires.

BACKGROUND OF THE INVENTION

An emerging technology in diagnostic catheters is conversion from reliance upon external sensors to use of in vivo sensors located within the body. Present technology often uses individual wires to connect the sensor, located in the catheter's distal end, to a connector located on the proximal end. Such interconnect methods are difficult to work with, hence can be costly in both yield loss and labor time.

Interconnect products currently available, such as conventional ribbon cable and parallel bonded magnet wire, do not meet the requirements for use as diagnostic catheter interconnects.

BRIEF DESCRIPTION OF THE INVENTION

The micro-cable interconnect of the present invention comprises a single exterior insulative flexible coating internally containing a plurality of terminally prepared, precisely spaced conductors. The conductors are arranged with a spacing and pitch to identically match spacing and pitch of interconnect zones operatively connected to an integrated circuit or connector, with the conductors constructed and arranged for bonding to the interconnect zones.

A method of forming a micro-cable interconnect comprises the steps of:

(a) providing a continuous formation of a plurality of conductors under tension;

(b) cleaning the conductors of step (a) to provide a uniform receptive surface for application of synthetic resin coating precursor;

(c) providing precisely controlled spacing and tension for the formation of cleaned conductors of step (b), to identically match the spacing of interconnect zones operatively connected to an integrated circuit or connector to which the conductors are constructed and arranged for attachment; (d) applying synthetic resin coating precursor to the formation of cleaned conductor wires of precisely controlled spacing and tension of step (c) and providing appropriate curing to selected areas of the coating precursor to provide cured and uncured portions of coating;

(e) removing uncured portions of coating, for example, by solvent spray or laser ablation; and (f) cutting the coated conductors of step (d) at the portions of removed uncured coating of step (e) to form lengths of micro-cable interconnect.

BRIEF DESCRIPTION OF THE DRAWINGS

FIG. 2 is a functional diagram of the construction apparatus employed in construction of the micro-cable interconnect of the present invention.

FIG. 3 is a perspective view of the micro-cable interconnect, retained within a catheter lumen, in assembly between a sensor and a connector.

FIG. 6 is a perspective detail of a fixed guide assembly.

FIG. 7 is a perspective detail of a moving guide assembly.

FIG. 10 is a fragmentary detail of a micro-cable interconnect with a stacked conductor formation.

FIG. 11 is a fragmentary detail of a micro-cable interconnect with a twisted conductor formation.

FIG. 12 is a fragmentary detail of a micro-cable interconnect, showing a formation with conductors in combination with micro-tubes.

DETAILED DESCRIPTION OF THE INVENTION

Figure 1:
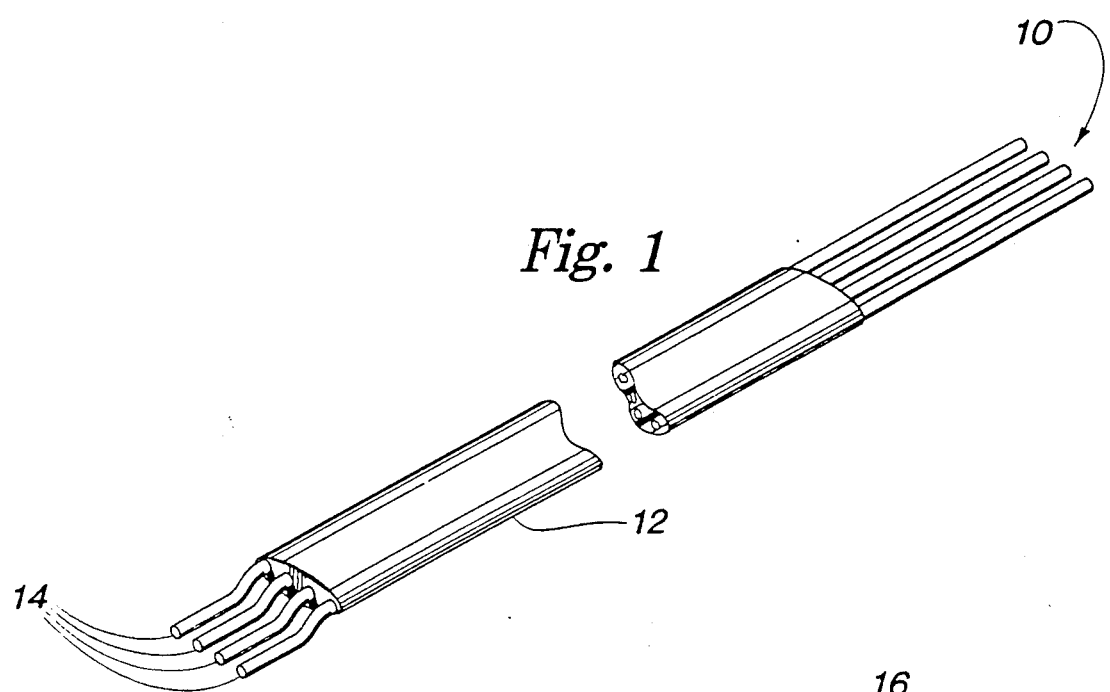
FIG. 1 is a perspective foreshortened view of the micro-cable interconnect of the present invention.
Figure 4:
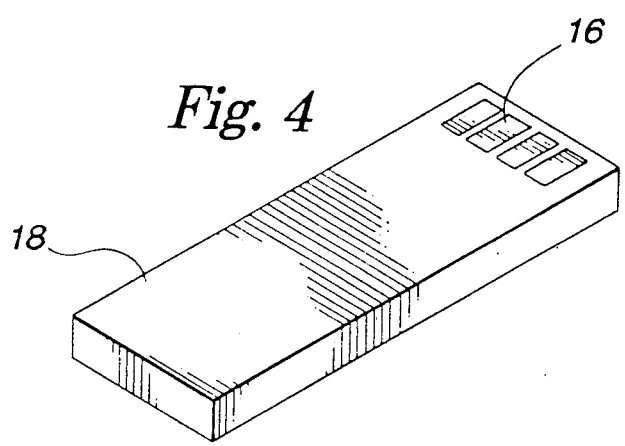
FIG. 4 is a detail perspective view of a sensor, showing pads for connection to the micro-cable interconnect.
Figure 5:
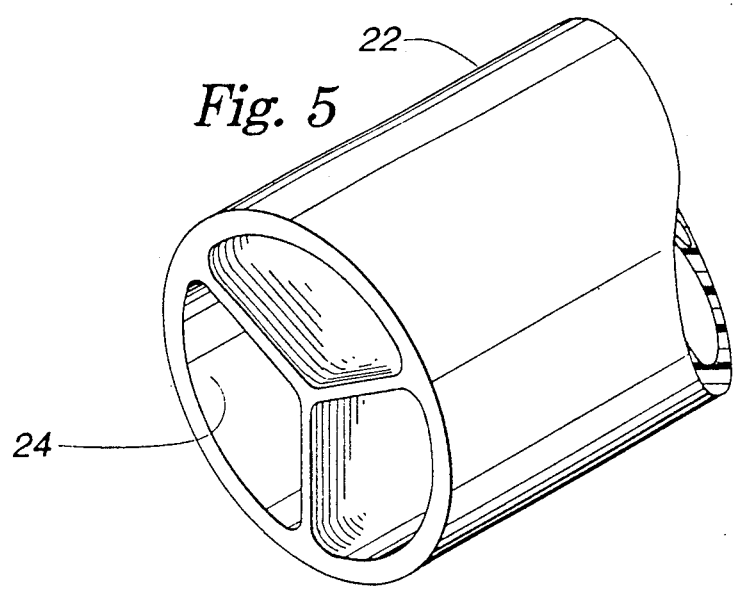
FIG. 5 is a fragmentary perspective detail view of a catheter.

A micro-cable interconnect 10 of the present invention is illustrated in FIGS. 1, 3 and 10-12. The micro-cable interconnect 10 comprises a single exterior insulative flexible coating 12 containing a plurality of terminally prepared precisely spaced conductors 14. The conductors 14 are arranged with a spacing and pitch to identically match the spacing and pitch of interconnect zones, for example, the interconnect zones 16, as shown in FIGS. 3 and 4, which are operatively connected to an integrated circuit or connector of a sensor 18. The conductors 14 are constructed and arranged for connection to the interconnect zones 16. The formation of the conductors 14 may be in a variety of forms, such as parallel co-planar, as shown in FIGS. 1 and 3, stacked, as shown in FIG. 10, twisted, as shown in FIG. 11, or conductors 14 in combination with micro-tubes 19, as shown in FIG. 12. The connection may be permanent, for example, by soldering or spot welding, or may be a removable plug-type connection The interconnect zones 16 may be contacts such as pins, pads, sockets, and the like and may in a preferred embodiment be conductive pads positioned on the sensor 18 substrate and connected to various circuit terminals within the sensor circuitry.

As illustrated in FIG. 3, the micro-cable interconnect 10 can be used to connect an integrated circuit or connector of a sensor 18, located at a distal end 20 of a catheter 22. In a preferred embodiment, the integrated circuit or connector of the sensor 18 is adapted and designed for in vivo sensing of certain body parameters and providing an output signal, which can be electrical, optical or a combination thereof, to the interconnect zones 16. The exterior insulative flexible coating 12 of the micro-cable interconnect 10 is non-toxic, bio-compatible and suitable for sterilization, and is adapted and designed for insertion within the catheter 22 lumen. The micro-cable interconnect 10 is further adapted and designed for coupling the output electrical or optical signal of the integrated circuit or connector of the sensor 18 to a connector 25 at a proximal end 24 of the catheter 22, for sensing, receiving and transmitting information regarding body parameters, such as electrical information, optical information or a combination thereof, depending on the type of output signal provided. The conductors 14, for providing electrical and/or optical sensing, are well-known in the art and are typically formed of metal wire, such as copper, gold- or silver-plated copper, or aluminum, or optical glass fiber.

Alternatively, the conductors 14, instead of being electrical or optical conductors as just described, may be micro-tubes 19, as illustrated in FIG. 12, in which embodiment, the micro-cable interconnect would provide operative connection for transmission of pressure control to in-body sensors, for injecting bio-compatible fluids, or for sensing in-body pressure conditions. When the conductors 14 are micro-tubes 19, they are formed of materials known in the art which are non-toxic, bio-compatible and suitable for sterilization, such as polyimides. It is to be understood that, in the following description of the micro-cable interconnect, the method of preparation and in the claims, whenever conductors 14 are referred to, this is intended to also refer to micro-tubes 19 or to a combination of conductors 14 and micro-tubes 19.

The conductors 14 (and/or micro-tubes 19) can be arranged in the micro-cable interconnect 10 in a co-planar parallel array, as illustrated in FIGS. 1 and 3, or in a stacked array (FIG. 10), a twisted array (FIG. 11), or in combination with micro-tubes 19 (FIG. 12). The number of conductors 14/micro-tubes 19 is of course based on the intended usage of the micro-cable interconnect 10 and typically varies from two to five or more.

The coating 12 is formed of a flexible synthetic resin coating, preferably an ultraviolet curable coating. The conductors 14, whether for providing electrical and/or optical sensing, or micro-tubes 19, generally have a cross-sectional diameter of about 0.001 to 0.006 inches and an interconductor spacing of about 0.001 to 0.007 inches. Specific dimensions for the micro-cable interconnect 10 are based on the required number, spacing and pitch of conductors 14/micro-tubes 19, and would typically include a width of about 0.016 to 0.030 inches and a thickness of about 0.006 to 0.010 inches. A typical four conductor micro-cable interconnect (about 0.002 inch diameter with conductors spaced 0.004 inch on center) is about 0.016 inch wide.

A schematic illustration of an apparatus 26 for carrying out the method of forming the micro-cable interconnect 10 of the present invention is provided in FIG. 2. A continuous formation of a plurality of conductors 14 is supplied from spools 30 under uniform tension in spool unwind station 32. Usually four to eight spools 30 are used, depending on the number of conductors 14 desired in the micro-cable interconnect 10. Supply tension is controlled by using magnetic clutch assemblies to restrict rotation of the spools 30.

The formation of conductors 14 travel from the supply station 32 to spray cleaning station 34, where spray cleaning 36 of the conductors 14 provides a uniform receptive surface for application of synthetic resin coating precursor. The spray cleaning station 34 consists of several sections, typically about five. The first section contains a chemical cleaner spray. A suitable cleaner has been found to be a surfactant detergent, such as Det-0-Jet, available from Alconox, Inc. 215 Park Ave. New York, NY, typically used at a concentration of 1 oz. per gallon of water and a temperature of about 150° F. This first section is designed to remove organic contamination, such as oils, grease, etc. The last four spray sections contain DI water. Pure DI water is pumped into section 5, and the water is allowed to cascade down to section 2. The water overflow from section 2 goes to a drain. These DI water spray rinses remove residual contamination, as well as chemical cleaner. The DI water is cascaded to assure the purest water is available in the final spray rinse, while minimizing water consumption.

The conductors 14 then travel from the cleaning station 34 to alignment station 38, where precisely controlled spacing and tension is provided to the conductors 14 to identically match the spacing and pitch of interconnect zones 16 operatively connected to an integrated circuit or connector of a specific sensor 18. The purpose of this station 38 is to establish the conductor 14 spacing and test the tension before synthetic resin coating precursor is applied. The tension is measured in grams by a tension sensor. One sensor per conductor 14 is preferably used. A presort guide keeps the general spacing between the conductors 14, while tension is being measured, and also acts as a preguide for the conductors 14 going into the moving guide assembly, as will be described hereinafter. A fixed guide assembly 39, as shown in FIG. 6, establishes the spacing for the mid-section of the micro-cable interconnect 10, that is, the section intermediate the exposed terminal ends of the micro-cable interconnect 10. The fixed guide assembly 39 is made up of shims 46 with precise thickness dimensions, laminated together with varying thicknesses to establish precision slots within the laminate. As the conductors 14 leave the fixed guide assembly 39, they pass over planarity guide pin 47 which serves to maintain the planarity and correct tension of the conductor 14 array.

Figure 8:
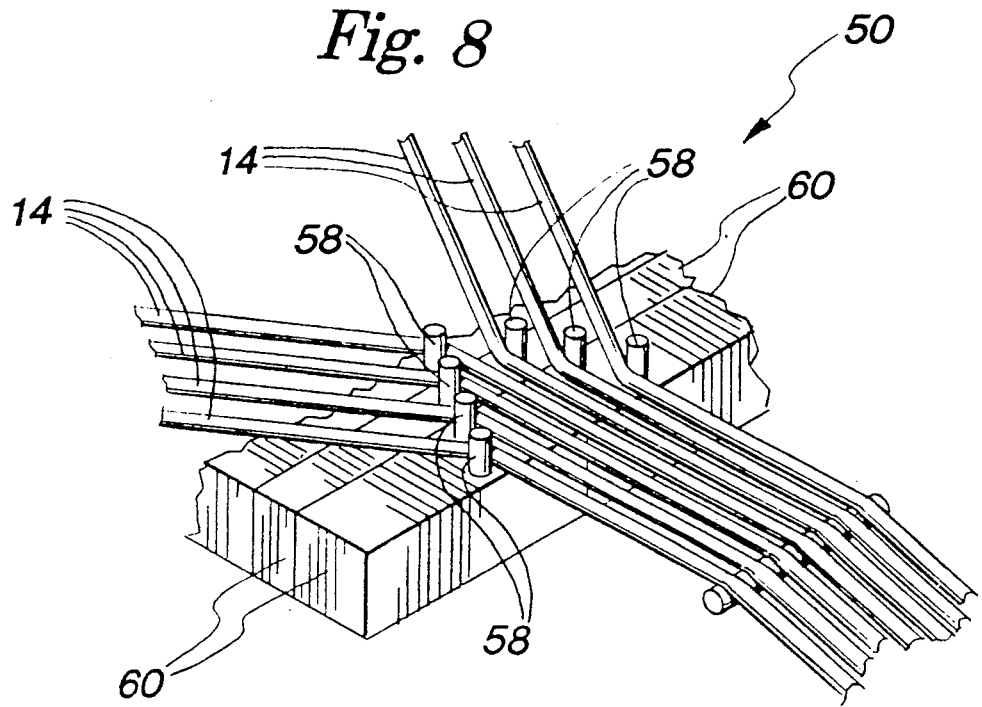
FIG. 8 is a perspective detail of an alternate guide assembly.
Figure 9:
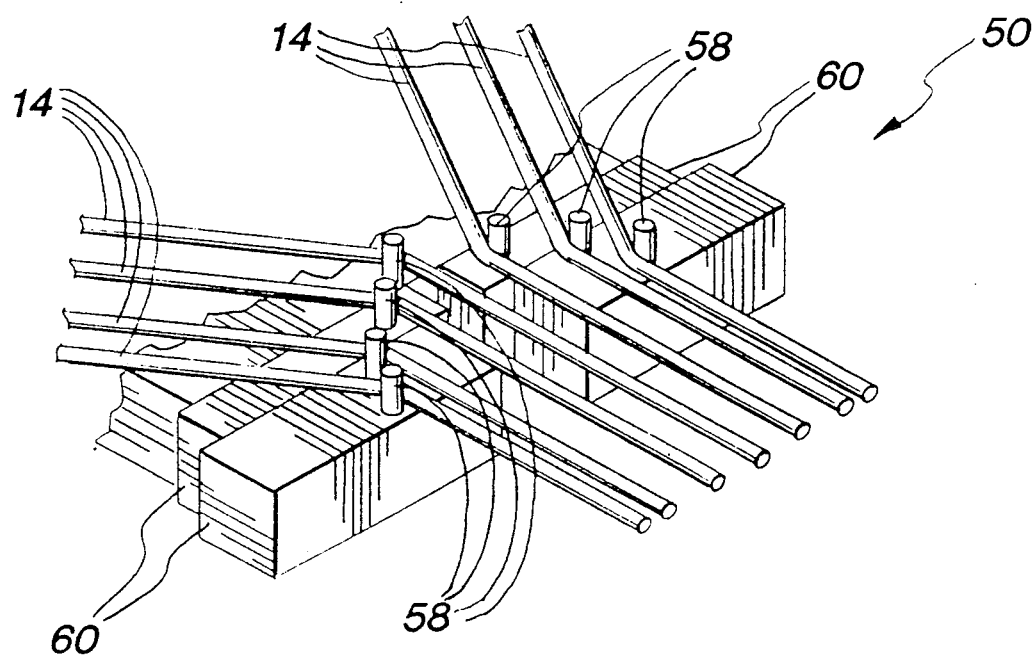
FIG. 9 is a perspective detail of the alternate guide assembly of FIG. 8 in slideable operation.

A moving guide assembly 48, 50, as illustrated by alternate forms in FIGS. 7, 8 and 9, is used to establish the inter-conductor spacing for the fanned end of the micro-cable interconnect 10. This fanned end is designed to match the spacing and pitch requirements of various interconnect zones 16 of specific integrated circuits or connectors 18. The moving guide assembly 48, 50 can be according to either of two different concepts. Concept one, illustrated in FIG. 7, utilizes a guide plate 54 with slots 56 at acute angles to each other that form a fan out array. Planarity guide pin 57 holds conductors 14 motionless in the direction perpendicular to the fan out, as the guide plate 54 is moved up or down to increase or decrease conductor to conductor separation. Concept two, illustrated in FIGS. 8 and 9, involves the independent movement of each of the individual conductors 14 that need to be fanned out. Each conductor 14 is moved linearly by a small pin 58 mounted on a slideable shaft 60, as shown in FIG. 9. The motion of each shaft 60 is directed by an assembly of linkages, not shown, that are digitally controlled by a linear table. Planarity guide pin 57, illustrated in FIG. 8, maintains planarity and correct tension of the conductor 14 array.

The conductors 14 then travel from the alignment station 38 to the coating application, curing and uncured coating removal station 40 where synthetic resin coating precursor is applied to the conductors 14, and subsequently, appropriate curing is applied to selected areas of the coating to provide cured and uncured portions. The coating precursor is applied to the conductors 14 by any suitable method, such as by a droplet application method. A coating precursor applicator 62 is positioned over the conductors 14. Coating precursor is dispensed slowly through an applicator needle forming a droplet. The droplet diameter is controlled by needle diameter, coating precursor viscosity and application pressure. The droplet should be larger than the total width of the aligned conductor 14 formation. The droplet is brought into contact with the moving conductors 14 forming a suspended coating precursor bath. An appropriate magnetic field may be applied to lateral exterior edges of the conductor 14 array as the droplet of coating precursor is being applied to "draw out" the droplet laterally forming an oval-shaped profile to the final cured coating 12 (as can be seen in FIGS. 1, 3 and 10–12). This serves to minimize the amount of coating precursor required to form an effective insulative flexible coating 12 for the micro-cable interconnect 10. The micro-cable interconnect coating 12 thickness is dependent on wire and wire-to-wire characteristics.

As will be obvious to those of skill in this art, any method which will provide coated and uncoated sections of conductors 14 may be used, for example, applying coating precursor to only certain sections of conductors 14 followed by appropriate curing.

Curing of the coating is conducted by any method appropriate to the selected coating precursor, for example, as follows. A mercury vapor UV lamp 64 with a peak output wavelength of 365 nm is used as the light source. The light is transmitted through a liquid optic cable. The light is shuttered using a slide mechanism that moves in and out of the light path. Shuttering the light creates unexposed coating sections that will be removed later. The removal of unexposed coating is accomplished by solvent spray 66 or by bath immersion to wash away uncured coating. Any residual particles are removed by spraying hot DI water over the washed area.

The conductors 14 then travel from the coating application, curing and uncured coating removal station 40 to the inspection and final cure station 42. The continuous line of micro-cable interconnect is inspected for conductor alignment and coating dimensions and integrity. An in-line optical sensing system 68 is used, with the sensing head focused on the moving conductor. Background lighting may be used as required. Cable attributes monitored are conductor spacing, conductor planarity, conductor continuity, coating consistency and coating edge quality. If a final cure of the coating is required, the continuous line of micro-cable interconnect is moved through an appropriate curing section, such as a UV cavity to complete the coating curing process.

The conductors 14 then travel from the inspection and final cure station 42 to the cable drive and cutting station 44. Drive rollers 72 pull the continuous line of micro-cable interconnect through the entire processing apparatus 26. A standard motor control is used to drive a DC or servo motor at varied, controlled speeds. The motor is linked to a pair of rollers 72. The roller 72 surface is coated with a pliable material that conforms to and grips the cable. The rollers 72 pull the cable through the process and push it into the cutters 74. A shearing die is used to cut the cable. The cable is fed through a guide to properly position the cable into the shearing die, where it is cut through the areas from which the coating has been removed, thus forming the individual sections of micro-cable interconnect 10.

To additionally minimize the amount of coating on the final micro-cable interconnect 10 while maximizing the effective insulative flexible properties, it may be desirable to provide "sacrificial" conductors 14 at the lateral exterior edges of the conductor 14 array. After the coating has been applied and cured, these "sacrificial" conductors 14 can be linearly cut away from the body of the continuous length of micro-cable interconnect, forming a laterally truncated oval profile to the micro-cable interconnect 10.

It is to be understood that, although the micro-cable interconnect of this invention has been specifically described with reference to use for providing interconnection of diagnostic catheters, it is equally well suited to use in any applications requiring micro-interconnection for electrical, optical, fluid or other appropriate applications. Specifically, the micro-cable interconnect may be used to provide interconnection in semi-conductor applications, telecommunications and other electrical, optical and fluid micro-interconnections.

What which is claimed is:

1. A method of forming a micro-cable interconnect comprising the steps of:
   (a) providing a continuous formation of conductors of precisely controlled spacing and tension to identically match spacing of interconnect zones operatively connected to an integrated circuit or connector to which said conductors are constructed and arranged for attachment;
   (b) applying synthetic resin coating precursor to selected lengths of said formation of conductors and providing curing to said selected lengths to provide cured and uncured portions; and
   (c) cutting said conductors at said uncured portions to form micro-cable interconnect adapted and arranged for connection to said connector or to said integrated circuit.

2. A method according to claim 1, wherein cured and uncured portions are formed in step (b) by applying UV curable coating precursor to said continuous formation of conductors, providing UV curing to selected areas of said coating precursor to provide cured and uncured coating portions, and removing uncured portions of coating 3. A method according to claim 1, additionally comprising pre-cleaning the conductor wires prior to step (a) to provide a uniform receptive surface for application of coating precursor.

4. A method according to claim 3, wherein pre-cleaning comprises passing the conductor wires through a first cleaning section for removal of organic contamination, followed by DI water rinse.

5. A method according to claim 2, wherein tension is provided by tension sensors for each conductor and spacing is provided by a fixed guide assembly to establish spacing for a mid-section of micro-cable interconnect and by a moving guide assembly to establish spacing for a fanned array at a terminal end of micro-cable interconnect.

6. A method according to claim 5, wherein the fixed guide assembly is made of shims with precise thickness dimensions, laminated together to form a laminate with varying thicknesses to establish precision slots within the laminate.

7. A method according to claim 5, wherein the moving guide is formed of a guide plate with slots at acute angles to each other to guide the conductors into a fanned array and guide pins to hold the conductors in a direction perpendicular to the fanned array.

8. A method according to claim 5, wherein the moving guide comprises means for moving each conductor linearly responsive to digital control.

9. A method according to claim 1, wherein in step (b) the coating precursor application is by an dispensing the coating precursor onto the conductor wire droplets and curing is b UV irradiation.

10. A method according to claim 1, additionally comprising providing inspection for conductor spacing, planarity, continuity, coating consistency and coating edge quality, and optionally, final coating curing, immediately prior to step (c).

* * * * *